US010996209B2

(12) United States Patent
Ben Amara et al.

(10) Patent No.: US 10,996,209 B2
(45) Date of Patent: May 4, 2021

(54) DEVICE FOR ANALYSING THE SENSITIVITY TO THE FORMATION OF DEPOSIT IN A FUEL, IN PARTICULAR A FUEL USED IN AIRCRAFT

(71) Applicant: IFP Energies nouvelles, Rueil-Malmaison (FR)

(72) Inventors: Arij Ben Amara, Le Pecq (FR); Maira Alves Fortunato, Carrieres sur Seine (FR); Laurie Starck, Rueil Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 201 days.

(21) Appl. No.: 16/077,278

(22) PCT Filed: Jan. 30, 2017

(86) PCT No.: PCT/EP2017/051929
§ 371 (c)(1),
(2) Date: Aug. 10, 2018

(87) PCT Pub. No.: WO2017/137274
PCT Pub. Date: Aug. 17, 2017

(65) Prior Publication Data
US 2019/0049424 A1 Feb. 14, 2019

(30) Foreign Application Priority Data
Feb. 11, 2016 (FR) ...................... 1651086

(51) Int. Cl.
*G01N 33/28* (2006.01)

(52) U.S. Cl.
CPC .............................. *G01N 33/2805* (2013.01)

(58) Field of Classification Search
CPC ................................................. G01N 33/2805
See application file for complete search history.

(56) References Cited

U.S. PATENT DOCUMENTS

| 5,293,218 A | 3/1994 | Morris et al. |
| 5,337,599 A | 8/1994 | Hundere et al. |
| 2012/0014409 A1 | 1/2012 | Youngblood et al. |

FOREIGN PATENT DOCUMENTS

| GB | 2281620 A | 3/1995 |
| GB | 2292607 A | 2/1996 |

OTHER PUBLICATIONS

International Search Report for PCT/EP2017/051929, dated Feb. 16, 2017; English translation submitted herewith (7 pgs.).

*Primary Examiner* — David Z Huang
(74) *Attorney, Agent, or Firm* — Fitch, Even, Tabin & Flannery LLP

(57) ABSTRACT

The present invention is a device for analyzing sensitivity to deposit formation in a fuel notably used in aircraft, comprising a tank (10) for the fuel to be analysed, at least one test section (18) with a heated tube (46) along which the fuel flows and a filter (66) associated with a deposit measurement system (68). According to the invention, the device comprises at least two identical test sections (18$_1$ to 18$_6$) arranged in parallel and a control unit (72) independently controlling at least one of the operating conditions of at least one of the two test sections.

21 Claims, 1 Drawing Sheet

DEVICE FOR ANALYSING THE SENSITIVITY TO THE FORMATION OF DEPOSIT IN A FUEL, IN PARTICULAR A FUEL USED IN AIRCRAFT

Reference is made to PCT/EP2017/051929 filed Jan. 30, 2017, and French Application No. 16/51.086 filed Feb. 11, 2016, which are incorporated herein by reference in their entirety.

BACKGROUND OF THE INVENTION

Field of the Invention

The present invention relates to a device for analysing a fuel, notably fuel used in aircraft, such as jet fuel. It more particularly relates to a device for analysing sensitivity of jet fuel to formation of deposits over a wide range of temperatures and operating conditions (fuel flow rate, metallurgy, residence time).

The stability of j et fuel has aroused significant interest from the aviation industry. This is due, on the one hand, to increasing thermal and rheological constraints of new combustion systems and, on the other hand, to the diversified fuels and methods that are used.

Furthermore, alternative jet fuels receive special attention as vectors of energy diversity and reduction of the environmental impact of air transport.

These novel jet fuels however involve new physico-chemical properties likely to impact the thermo-oxidative stability of these jet fuels.

Description of the Prior Art

A method for qualification of the thermal stability of jet fuels known as "Jet Fuel Thermal Oxidation tester" (JF-TOT), an example of which is illustrated in U.S. Pat. No. 5,293,218, circulates jet fuel around a heated tube.

This method quantifies jet fuels according to two parameters:
(1) Formation of particles in the fluid, measured with a pressure difference through a filter (DP filter); and
(2) Evaluation of solid deposits formed on the test tube, by visual or quantitative evaluation.

The test is carried out at 260° C. on conventional jet fuels, at 325° C. for alternative jet fuels of SPK type (Synthetic Paraffinic Kerosene) and at 355° C. for jet fuels of SIP type (Synthesized Iso-Paraffin). These temperatures are defined in the ASTM certification process by the players in the field (petroleum engineers, engine manufacturers . . . ).

This diversity of certification temperatures clearly shows the need to know the sensitivity of a jet fuel to deposit formation depending on the temperature.

The details of this procedure are best described in the ASTM D3241-14be1 standard method (Standard Test Method for Thermal Oxidation Stability of Aviation Turbine Fuels, 2014).

It has been found that temperature is a key factor in the thermo-oxidative degradation of fuels, the formation of deposits, and the type of deposit thus formed.

Distinction is made within this context between the auto-oxidation regime, generally between 100° C. and 350° C., the pyrolytic regime which involves thermal or catalytic cracking and polymerization reactions, above 400° C., and a transition phase that involves both regimes simultaneously.

FIG. 1 shows a typical profile of deposit formation (D) as a function of the temperature (° C.) of two jet fuels Fuel 1 and Fuel 2. Profile Fuel 1 is a typical profile of a conventional jet fuel and profile Fuel 2 is the representation of a typical profile of an alternative HEFA-SPK (Hydrotreated Esters and Fatty Acids—Synthetic Paraffinic Kerosine) jet fuel.

As can be seen in the figure, conventional jet fuel Fuel 1 has an auto-oxidation regime between 200° C. and 300° C., and a pyrolytic regime from 425° C., whereas alternative jet fuel Fuel 2 has an auto-oxidation regime between 100° C. and 250° C., and a pyrolytic regime from 325° C.

Regarding the circuit followed by the jet fuel in the aircraft, what is important to control is susceptibility to deposit formation at low and medium temperatures, therefore below approximately 400° C. Thus, for jet fuel Fuel 1, the deposit level increases between around 200° C. and 300° C., where it reaches a maximum level. The specification test carried out at 260° C. is favorably representative of the regime where the amount of deposit increases with temperature. On the other hand, for Fuel 2, the deposit level increases at a lower temperature. It reaches a maximum level at around 200° C. Thus, measurement of the specification test carried out at 325° C. does not represent the deposit formation at lower temperature levels.

Thus, it can be observed that the chemical composition of the jet fuel impacts these thermo-oxidative degradation regimes and, consequently, the morphology of the deposit and the characteristics thereof. Therefore, evaluating the thermal stability at a single temperature seems to be limited or even obsolete.

To overcome this, it is necessary to evaluate the jet fuel behavior over a much wider temperature range, therefore more representative of real conditions.

SUMMARY OF THE INVENTION

The present invention thus is a device for analysing the sensitivity to deposit formation in a fuel, notably a fuel used in aircraft, comprising a tank for the fuel to be analysed, at least one test section with a heated tube along which the fuel flows and a filter associated with a deposit measurement system, characterized in that it comprises at least two identical test sections arranged in parallel and a control unit independently controlling at least one of the operating conditions of at least one of the two test sections.

One of the operating conditions can be the temperature variation of the heated tube.

One of the operating conditions can be the flow rate variation of the fuel flowing along the heated tube.

One of the operating conditions can be the duration variation of the test section analysis.

One of the operating conditions can be the characteristics variation of the heated tube.

The characteristics of the tube can comprise the material of the tube or a surface condition of the tube.

The fuel can be a jet fuel, a diesel fuel or a gasoline fuel.

The invention also relates to a method for analysing the sensitivity to deposit formation in a fuel, notably a fuel used in aircraft, wherein the fuel to be analysed is circulated from a tank to at least one test section with a heated tube and a filter associated with a deposit measurement system. The fuel to be analysed is circulated in at least two identical test sections arranged in parallel and comprises an independent step of controlling at least one of the operating conditions of at least one of the two test sections.

BRIEF DESCRIPTION OF THE DRAWINGS

Other features and advantages of the invention will be clear from reading the description hereafter, given by way of non-limitative example, with reference to the accompanying figures wherein, in addition to FIG. 1 described above.

DETAILED DESCRIPTION OF THE INVENTION

Figure 1:
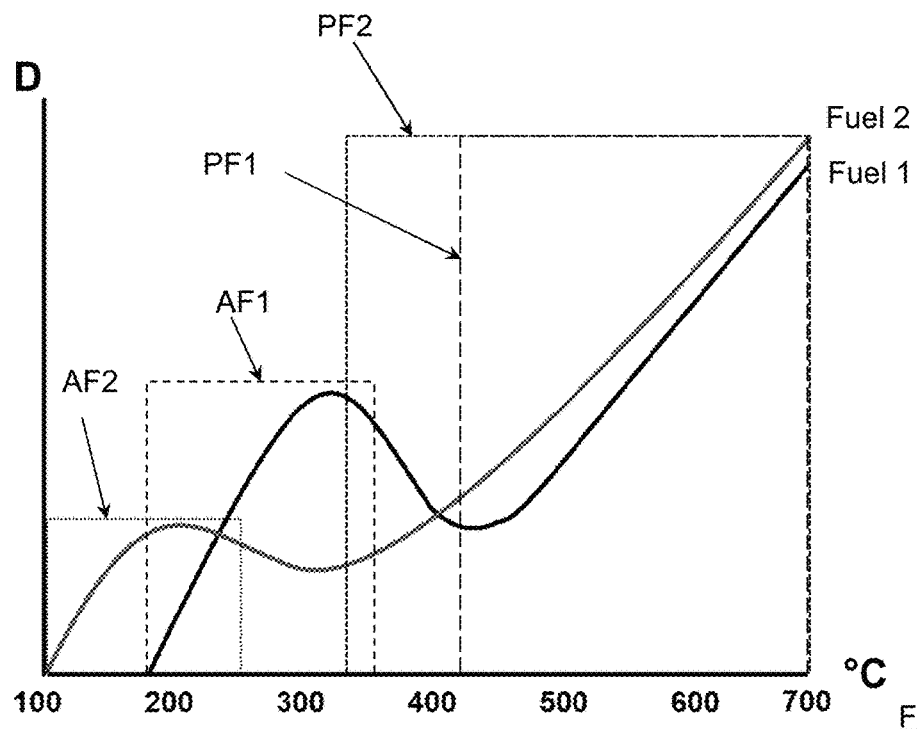
Figure 2:
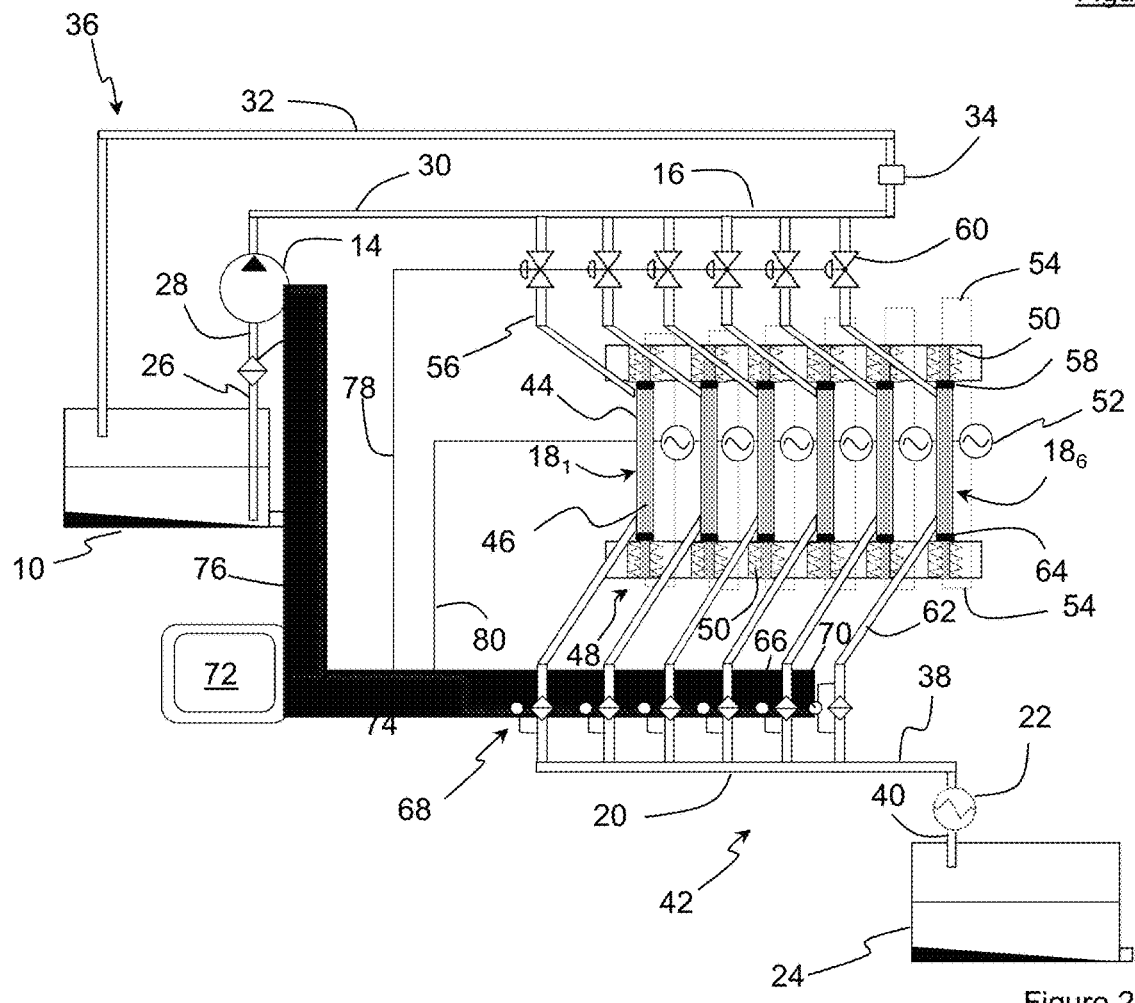
FIG. 2 illustrates a fuel analysis device according to an embodiment of the invention, notably for a fuel used in aircraft or jet fuel.

In FIG. 2, the analysis device is a device according to an embodiment of the invention, with a dynamic circulation system for the fuel to be analysed, here a conventional or alternative jet fuel.

This device comprises a supply tank 10 containing the jet fuel, a filter 12 for the jet fuel leaving the tank and a circulation pump 14 for this jet fuel. This circuit also comprises a distribution rail 16 supplying pumped jet fuel to at least two test sections, here six sections 181 to 186 arranged in parallel, and a discharge rail 20 for the jet fuel which has flowed through the test sections.

Advantageously, this discharge rail is connected to a heat exchanger 22 arranged downstream from a used jet fuel recovery tank 24.

This circuit further comprises various jet fuel circulation pipes for connecting the elements of this circuit.

Thus, a pipe 26 connects tank 10 to filter 12, another pipe 28 connects the filter to pump 14, yet another pipe 30 connects the pump to distribution rail 16, and finally a return pipe 32 connects the distribution rail to the supply tank, this pipe comprising a flow regulator 34.

All these elements thus make up a supply circuit 36 for the test sections.

As is best seen in FIG. 2, discharge rail 20 is connected by a pipe 38 to exchanger 22 which itself is connected by a pipe 40 to the recovery tank, thus forming a discharge circuit 42 for the test sections.

Each test section comprises a vertical rigid duct 44 housing a metal tube 46 of smaller diameter, a heater 48, here in form of electric resistors 50 arranged at each end of the tube, for heating this tube to the same temperature, a power supply 52 for these resistors through conductors 54, a jet fuel delivery manifold 56 between distribution rail 16 and upper end 58 of duct 44, a flow rate control system 60 provided on the manifold, a jet fuel discharge manifold 62 connecting lower end 64 of duct 44 to discharge rail 20 and carrying a jet fuel filter 66, and a measurement system 68 for measuring the deposit from the jet fuel deposited on the filter.

Preferably, this measurement system comprises a differential pressure sensor 70 for measuring the pressure differential between upstream and downstream of this filter.

This device also comprises a control unit 72 which controls independently at least one of the operating conditions of at least one of the two test sections, notably the temperature of the tubes, as well as automatic implementation of the analysis, which data is recorded in real time.

More particularly, this unit is connected by a control line 74 to differential sensor 70 to know the filter clogging state, by a control line 76 to circulation pump 14, by another control line 78 to flow rate control system 60 and by yet another control line 80 to resistor power supply 52.

In operation, control unit 72 controls independently at least one and preferably each heater 48 of tubes 46. The heating temperature of each tube can be separately regulated between 100° C. and 400° C. for each test section. Pump 14 extracts the jet fuel from tank 10 and passes it through filter 12. At the pump outlet, the jet fuel is sent to distribution rail 16 to feed all the delivery manifolds 56 of test sections 181 to 186. The flow rate of the jet fuel circulating in each manifold 56 is controlled independently by flow rate control system 60 managed by control unit 72.

From the manifold, the jet fuel passes into rigid duct 44 and circulates all along the outer wall of tube 46. Under the effect of the heat of this tube, deposits form from this jet fuel, part of which settles on this outer wall and another part mixes with the jet fuel.

The jet fuel and the dissolved deposits it contains are discharged through discharge manifold 62 towards recovery tank 24.

During this discharge, the jet fuel flows through filter 66 which retains the deposits contained in this jet fuel, then the jet fuel is cooled to around 20° C. by exchanger 22 prior to entering the recovery tank.

The excess jet fuel at distribution rail 16 is sent back to supply tank 10 through pipe 32.

The analysis is stopped after a given time period that can be defined separately for each test section.

It should be noted that the pressure differential through each filter 66 is monitored in real time by the associated differential pressure sensor 70, which indicates the formation of degradation products in the liquid fuel.

Furthermore, the solid deposits formed on the tubes can be characterized in terms of thickness and volume, either ex situ, with a quantification method, for example interferometry or ellipsometry as described in the ASTM D 3241 standard, or in situ, using transparent rigid ducts allowing light beam passage, coupled with an optical method, for example interferometry or ellipsometry as described in the ASTM D 3241 standard.

As illustrated by the example below, the device described above allows automatic control of the test. It reproduces under dynamic conditions deposits on several sections arranged in parallel which are subjected to different operating conditions.

Characterization of the fuel involves all or part of the following variations:

1) Temperature variation: The test is carried out at several temperatures on each test section. The recommended temperature Ti ranges between 160° C. and 360° C. The variation is preferably performed on at least five different test sections, all other things being equal: Duration Di (recommended duration 2.5 h), surface condition Wi (recommended Wi compatible with ASTM D 3241), fuel flow rate φi (recommended φi 3 mL/min).

2) Fuel flow rate variation: the recommended flow rate ranges between 0 and 30 mL/min. The variation is preferably performed on at least two different test sections, all other things being equal: Temperature Ti (recommended Ti 260° C.), duration Di (recommended duration 2.5 h), surface condition Wi (recommended Wi compatible with ASTM D 3241).

3) Test duration variation: The recommended duration Di ranges between 0 and 30 hours. The variation is preferably performed on at least two different test sections, all other things being equal: Temperature Ti (recommended Ti 260° C.), fuel flow rate φi (recommended φi 3 mL/min) and surface condition Wi (recommended Wi compatible with ASTM D 3241).

4) Tube characteristics variation: Non-standard tubes can be evaluated. These tubes can have different types of materials, coatings or surface conditions. For example, through the use of material having a catalytic function, such as copper, zinc and iron. The variation is preferably performed on at least two different test sections, all other things being equal: Temperature Ti (recommended Ti 260° C.), fuel flow rate φi (recommended φi 3 mL/min) and duration Di (recommended Di 2.5 h).

At the end of each analysis, the deposit formed on tubes 46 is characterized by a quantification method (the ASTM D 3241 methods for example).

Advantageously, an analysis module allows grouping the results of all the sections. The module then constructs the deposit amount variation curves as a function of the evaluated parameters, which are temperature, analysis duration, velocity of flow and surface characteristics. These various curves allow full mapping of the thermal stability of the jet fuel.

Thus, this mapping provides:

An analysis of the effect of key parameters on deposit formation a predictive tool allowing:
   Estimation of the stability of a jet fuel at all the untested intermediate temperatures, and
   Estimation of the breakpoint temperature a preventive tool for alerting the user of any default risk by associating the mapped data with the dimensions and the user's operating conditions.

The present invention is not limited to the example described above and it can apply to any type of fuel other than jet fuels.

In particular, the analysed fuel can be diesel fuel, biodiesel, gasoline, etc.

The invention claimed is:

1. A device for analyzing sensitivity of fuel to fuel deposit formation, comprising a tank for containing the fuel to be analyzed for fuel deposit formation, a filter for filtering fuel leaving the tank and a pump for circulating the fuel to leave the tank for sensitivity analysis, a distribution rail supplied with fuel circulated from the tank, at least two fuel test sections arranged in parallel through which the fuel flows which is supplied from the distribution rail, a discharge rail for fuel which has flowed through the at least two fuel test sections, a heat exchanger connected to the discharge rail for heating the fuel, a fuel recovery tank downstream from the heat exchanger, and a control unit which independently controls at least one operating condition of at least one of the at least two fuel test sections, each fuel test section comprising a vertical rigid duct housing at least one heated metal tube, a fuel delivery manifold between the distribution rail and an upper end of the vertical rigid duct, a flow rate control system provided with the fuel delivery manifold, a fuel discharge manifold connecting a lower end of the vertical rigid duct to the discharge rail and a fuel filter for carrying fuel deposits in fuel flowing from the fuel discharge manifold which is associated with a measurement system for measuring fuel deposits from the fuel on the fuel filter for carrying the fuel deposits.

2. An analysis device as claimed in claim 1, wherein the at least one operating condition is variation of temperature of the at least one heated metal tube.

3. A device as claimed in claim 2, wherein one of the at least one operating condition is variation of flow rate in the at least one heated metal tube.

4. A device as claimed in claim 3, wherein at least one of the at least one operating condition is variation in duration of testing in the at least two fuel test sections.

5. A device as claimed in claim 4, wherein one of the at least one operating condition is variation of at least one characteristic of the at least one heated metal tube.

6. A device as claimed in claim 3, wherein one of the at least one operating condition is variation of at least one characteristic of the at least one heated metal tube.

7. A device as claimed in claim 2, wherein at least one of the at least one operating condition is variation in duration of testing in the at least two fuel test sections.

8. A device as claimed in claim 7, wherein one of the at least one operating condition is variation of at least one characteristic of the at least one heated metal tube.

9. A device as claimed in claim 2, wherein one of the at least one operating condition is variation of at least one characteristic of the at least one heated metal tube.

10. A device as claimed in claim 1, wherein one of the at least one operating condition is variation of flow rate in the at least one heated metal tube.

11. A device as claimed in claim 10, wherein at least one of the at least one operating condition is variation in duration of testing in the at least two fuel test sections.

12. A device as claimed in claim 11, wherein one of the at least one operating condition is variation of at least one characteristic of the at least one heated metal tube.

13. A device as claimed in claim 10, wherein one of the at least one operating condition is variation of at least one characteristic of the at least one heated metal tube.

14. A device as claimed in claim 1, wherein at least one of the at least one operating condition is variation in duration of testing in the at least two fuel test sections.

15. A device as claimed in claim 14, wherein one of the at least one operating condition is variation of at least one characteristic of the at least one heated metal tube.

16. A device as claimed in claim 1, wherein one of the at least one operating condition is variation of at least one characteristic of the at least one heated metal tube.

17. A device as claimed in claim 16, wherein the at least one characteristic of the at least one heated metal tube comprises a material of the at least one heated metal tube or a surface condition of the at least one heated metal tube.

18. A device as claimed in claim 1, wherein the fuel is jet fuel.

19. A device as claimed in claim 1, wherein the fuel is diesel fuel.

20. A device as claimed in claim 1, wherein the fuel is gasoline.

21. A device as claimed in claim 1, wherein the deposit measurement system comprises a differential pressure sensor.

* * * * *